United States Patent [19]
Dooley et al.

[11] Patent Number: 5,942,440
[45] Date of Patent: Aug. 24, 1999

[54] METHOD FOR DETECTING ORGANIC CONTAMINANTS IN WATER SUPPLIES

[75] Inventors: Kirk J. Dooley, Shelley; Scott L. Barrie, Idaho Falls, both of Id.; William J. Buttner, White Bear Lake, Minn.

[73] Assignee: Lockheed Martin Idaho Technologies Company, Idaho Falls, Id.

[21] Appl. No.: 08/833,168

[22] Filed: Apr. 4, 1997

[51] Int. Cl.$^6$ ................................................ G01N 33/18
[52] U.S. Cl. ..................... 436/146; 73/64.56; 73/863.71; 73/864.73; 436/28; 436/125; 436/139; 436/178
[58] Field of Search ................................ 436/28, 125, 139, 436/145, 146, 177, 178, 181; 73/61.51, 61.55, 64.56, 683.71, 864.73, 866.5

[56] References Cited

U.S. PATENT DOCUMENTS 4,952,751  8/1990  Blume et al. .
5,100,555  3/1992  Matson .
5,167,825  12/1992  Lipski et al. .
5,472,613  12/1995  Schofield .

OTHER PUBLICATIONS

Schweitzer, Ed., Handbook of Separation Techniques for Chemical Engineers, McGraw Hill (1979) p. 2–67.
Chemical Abstracts No. 124:241565, Crowder et al. Proc. Int. Conf. Pervaporation Processes Chem. Ind., 7th (1995), pp. 106–117.
Chemical Abstracts No. 127:252733, Vroblesky et al. Ground Water Monit. Rem. (1997), 17(3), pp. 177–184.
Chemical Abstracts No. 118: 45302, Slivon et al., ACS Symp. Ser. (1992), 508 (Pollut. Prev. Ind. Processes), pp. 169–177.

Primary Examiner—Jan Ludlow
Attorney, Agent, or Firm—Klaas Law O'Meara & Malkin

[57] ABSTRACT

A system for detecting organic contaminants in water supplies. A sampling unit is employed which includes a housing having at least one opening therein and a tubular member positioned within the housing having a central passageway surrounded by a side wall. The side wall is made of a composition designed to absorb the contaminants. In use, the sampling unit is immersed in a water supply. The water supply contacts the tubular member through the opening in the housing, with any contaminants being absorbed into the side wall of the tubular member. A carrier gas is then passed through the central passageway of the tubular member. The contaminants will diffuse out of the side wall and into the central passageway where they will subsequently combine with the carrier gas, thereby yielding a gaseous product. The gaseous product is then analyzed to determine the amount and type of contaminants therein.

14 Claims, 5 Drawing Sheets

METHOD FOR DETECTING ORGANIC CONTAMINANTS IN WATER SUPPLIES

CONTRACTUAL ORIGIN OF THE INVENTION

The United States has rights in this invention pursuant to Contract No. DE-AC07-94ID13223 between the U.S. Department of Energy and Lockheed Martin Idaho Technologies Company.

BACKGROUND OF THE INVENTION

The present invention generally relates to pollutant detection, and more particularly to the analysis of water supplies for the measurement and characterization of organic contaminants therein.

The presence of organic contaminants in underground water supplies and other water sources can present significant pollution problems. A wide variety of organic materials may be present in subterranean water-containing regions, depending on how the overlying land under consideration has been used. For example, many different organic solvents and related compositions (e.g. both unhalogenated and halogenated compounds) may exist in groundwater supplies at factory sites and other locations where extensive use of these chemicals has occurred over long time periods. Such materials are typically characterized as "volatile organic contaminants (compounds)" or "VOCs". Of particular concern are halogenated (e.g. chlorinated) solvents including trichloroethane, dichloroethane, and others. However, in addition to halogenated solvents, a wide variety of other organic compositions shall be encompassed within the term "organic contaminants" as discussed below including but not limited to methane, vinyl chloride, ethane, ethene, benzene, toluene, xylene, and others. Of equal concern is the presence of petroleum-based fuels (e.g. jet fuel, gasoline, diesel fuel, and the like) in underground water-containing regions at various transportation-related facilities including but not limited to gasoline stations, airports, military bases, and the like. Regardless of the particular organic contaminants under consideration, the presence of these materials at or near underground or above-ground water supplies is a substantial problem of considerable importance. Accordingly, the present invention shall not be restricted to the analysis of any given organic compounds.

Many different methods have been used to analyze water supplies at various test sites. Of particular importance is the analysis of aquifers for high concentrations of organic waste products. The term "aquifer" as used herein basically involves a large underground water source located within vast regions of rock or soil. Prior testing methods have involved the drilling of deep wells directly into an underground water-containing site (e.g. an aquifer), followed by the placement of screening materials within the wells. Dedicated submersible pumps were then positioned in each well to withdraw numerous water samples for delivery to the well head. Thereafter, the samples were analyzed to determine the type and amount of organic contaminants in the samples.

While this method provided important information regarding the levels of organic contamination in the water supplies of concern, it did not supply any data involving the vertical distribution and "stratification" (e.g. three-dimensional location) of organic contamination in the water supplies. This type of data is important in determining the spatial distribution of organic contamination including how far (both vertically and horizontally) the contaminants have dispersed in the water source of concern. The testing methods described above are not "location sensitive" and provide little information concerning the specific three-dimensional distribution of organic contamination. Traditional testing methods also require a large amount of expensive equipment, are labor intensive, and involve complex operating procedures. Finally, conventional processes which require the removal of numerous liquid samples for individual testing typically generate large quantities of waste products (e.g. residual sample materials) which, if sufficiently contaminated, can present significant disposal problems. Prior to development of the present invention, a need therefore remained for an efficient testing system which avoids these disadvantages and enables underground water supplies (as well as above-ground water sources) to be tested in an accurate, rapid, and effective manner.

The claimed invention represents a unique and highly-efficient alternative to the methods listed above. It does not require extensive equipment (e.g. submersible pumps) and complex operating procedures. It can also analyze large water supplies without extracting any sample materials so that waste problems are avoided. Finally, the method and apparatus described below enable the water supply of interest to be simultaneously analyzed at multiple locations so that the contamination may be "mapped". Decontamination of the water source can then occur in a more site-specific and accurate manner. The present invention therefore involves a highly effective testing system which represents a substantial advance in the art of pollution detection and remediation as discussed further below.

SUMMARY OF THE INVENTION

It is an object of the present invention to provide a highly efficient testing method and apparatus which enables the quantitative and qualitative analysis of a water supply for organic contaminants.

It is another object of the invention to provide a method and apparatus for capturing a representative concentration of organic contaminants in water supplies which allows the analysis of a wide variety of different organic materials at varying levels.

It is another object of the invention to provide a method and apparatus for monitoring organic contaminants in water supplies which uses an operating system and procedure of minimal complexity.

It is another object of the invention to provide a method and apparatus for monitoring organic contaminants in water supplies which avoids the need for submersible pump systems.

It is a further object of the invention to provide a method and apparatus for monitoring organic contaminants in water supplies which is capable of effectively analyzing underground water-containing regions (e.g. aquifers) and above-ground water sources.

It is a further object of the invention to provide a method and apparatus for monitoring organic contaminants in water supplies which enables testing to take place without physically removing any water samples from the test area.

It is an even further object of the invention to provide a method and apparatus for monitoring organic contaminants in water supplies which avoids the generation of waste products (e.g. residual sample materials), and likewise eliminates the disposal problems associated therewith.

It is an even further object of the invention to provide a method and apparatus for monitoring organic contaminants in water supplies which is characterized by reduced labor requirements and processing times.

It is a still further object of the invention to provide a method and apparatus for monitoring organic contaminants in water supplies which enables a spatial distribution (e.g. a vertical or horizontal analysis) of the organic contaminants to be obtained.

It is a still further object of the invention to provide a method and apparatus for monitoring organic contaminants in water supplies which facilitates the mapping of organic contamination zones in a highly effective manner so that site-specific, high-efficiency remediation procedures may be initiated.

In accordance with the foregoing objects, the present invention involves a unique and efficient system which is able to test water supplies for the presence and quantity of organic contaminants therein. The method and apparatus described herein is equally applicable to both groundwater supplies (e.g. "aquifers" as discussed above), surface water regions (lakes, ponds, streams, rivers, creeks, etc.), and any other water-containing zones which need to be tested for organic contamination. Accordingly, the claimed invention shall not be limited to the testing of any particular bodies of water or water samples, and shall likewise not be restricted to the detection of any specific organic contaminants. The term "organic contaminant" shall encompass a broad spectrum of organic (carbon-based) compounds including but not limited to alkanes, alkenes, aryl compounds, esters, ethers, halogenated (e.g. chlorinated) derivatives of these materials, petroleum-based compounds (e.g. jet fuel or gasoline), and other comparable materials.

A brief overview of the present invention and its main features will now be provided. More specific details involving the claimed process and apparatus will be presented below in the Detailed Description of Preferred Embodiments section. In accordance with the invention, a specialized sampling unit is initially provided. Typically, the sampling unit is attached to an elongate, flexible rope-like member (e.g. made of braided metal [stainless steel] cable) so that it can be readily lowered into the water supply of interest. The sampling unit includes a housing (preferably tubular in configuration with a circular cross-section) having an outer wall and an internal cavity therein surrounded by the outer wall. The housing likewise has an upper end and a lower end. The outer wall of the housing further comprises at least one opening through the wall which enables fluid materials (e.g. the water being tested) to pass through the outer wall and into the internal cavity of the housing. Multiple openings may likewise be employed in the outer wall to create a uniformly-perforated structure. Preferred construction materials which are used to produce the sampling unit (e.g. housing), as well as the dimensions associated with the housing and other components of the sampling unit will also be provided in the Detailed Description of Preferred Embodiments section.

In a representative embodiment designed to produce optimum results, the sampling unit further includes an upper cap member operatively connected to the upper end of the housing and a lower cap member operatively connected to the lower end of the housing. The upper cap member comprises a gas delivery port therethrough. Likewise, the lower cap member includes a gas exit port which passes through the cap member. The function of these ports will be discussed further below.

Next, a tubular member is provided which is positioned inside the internal cavity of the housing. The tubular member includes an uninterrupted (e.g. non-perforated) side wall and a central passageway therein which is entirely surrounded by the side wall. The side wall has a preferred uniform thickness of about 0.0235–0.25 inches. This thickness level enables the tubular member to perform its intended function with an optimum degree of effectiveness. In addition, the tubular member includes a first end and a second end. The tubular member is constructed from at least one composition (preferably plastic) which is capable of absorbing organic contaminants directly into the side wall of the tubular member so that these materials are retained therein (on a temporary basis). In addition, the tubular member may be linear (e.g. straight) in configuration or helically-coiled. Helical coiling of the tubular member provides increased surface area for enhanced absorbance of the organic contaminants.

In the present embodiment which includes upper and lower cap members attached to the housing, the first end of the tubular member is operatively connected to the upper cap member so that the central passageway through the tubular member is in fluid communication with the gas delivery port in the upper cap member. Likewise, the second end of the tubular member is operatively connected to the lower cap member so that the central passageway through the tubular member is in fluid communication with the gas exit port. This design facilitates the controlled flow of gaseous materials (e.g. a carrier gas as listed below) into and through the tubular member during operation of the sampling unit. As previously noted, the composition used to produce the tubular member is constructed from a material which is capable of absorbing organic compositions directly into the side wall of the tubular member. While the claimed invention shall not be restricted to any particular compounds for this purpose, representative materials suitable for producing the tubular member include plastic and/or rubber-based materials selected from the group consisting of polydimethylsiloxane, polytetraflouroethylene (TEFLON®), natural rubber, "latex"-type rubber, polypropylene, polyethylene, nylon, and neoprene. These materials again provide the desired degree of affinity for the organic contaminants of concern, but are likewise able to release the organic contaminants by diffusion (e.g. "off-gassing") at an appropriate time in accordance with the reaction conditions specified below which are part of the claimed testing method.

Regardless of the particular design configuration associated with the sampling unit, its unique abilities are provided by the following inventive features: (A) the use of a contaminant-absorbing member which is capable of absorbing organic compounds directly into the contaminant-absorbing member; and (B) placement of the contaminant-absorbing member inside a protective housing having multiple water-entry openings through the housing. As a result, the claimed sampling unit is able to effectively detect and characterize organic contaminant levels in a water supply on an in situ basis using the claimed method which will now be summarized.

To analyze a water supply using the sampling unit listed above, the unit is directly immersed in the selected water supply. In the case of underground water sources (e.g. aquifers), the sampling unit is optimally lowered into the water through a well drilled into the ground. Either the first end or the second end of the housing associated with the sampling unit may be attached to an elongate, flexible rope-like member (optimally made of braided metal [stainless steel] cable) which is used to lower the sampling unit in position. After immersion of the sampling unit into the water supply (which is also generally characterized herein as a "water sample"), the water flows into the internal cavity of the housing through the opening or openings therethrough. As a result, the water comes in direct physical contact with the side wall of the tubular member inside the housing. Any organic contaminants in the water supply will then be absorbed into the interior regions of the side wall. This process occurs in accordance with the unique chemical and physical characteristics of the materials which are used to construct the tubular member. The organic contaminants are retained within the side wall of the tubular member on a temporary basis, and subsequently diffuse (e.g. "off-gas") out of the side wall at a rate which is dependent on numerous factors. These factors include the particular materials which are used to produce the tubular member, the specific organic contaminants in the water supply, "incubation" time in the water supply, and others. The released organic materials are then collected and analyzed in accordance with the unique steps in the remaining portions of the claimed process as outlined below.

In a preferred and non-limiting embodiment, the sampling unit is maintained within the water supply/sample for a time period of about 8–72 hours. This time period is sufficient in most cases to enable complete absorption of the organic contaminants into the side wall of the tubular member so that accurate test results are ensured. However, the time period listed above may be varied as needed in accordance with preliminary tests involving the particular materials used to manufacture the sampling unit and the water source under consideration. Thereafter, a supply of at least one carrier gas is delivered (e.g. passed/introduced) into and through the central passageway of the II tubular member in the sampling unit. Representative carrier gases include but are not limited to air, helium, nitrogen, argon, and oxygen. Gas delivery may occur while the sampling unit is still within the water supply or may take place after removal of the sampling unit from the water supply. In situations where the sampling unit is removed from the water supply for carrier gas delivery and further processing, an additional (optional) step may be taken to prevent to prevent premature desorption/diffusion of the organic contaminants from the side wall of the tubular member which may occur if the process is delayed at this point. To avoid this problem after removal of the sampling unit from the water source, the unit is placed within a fluid (liquid) storage medium prior to delivery of the carrier gas into the central passageway of the tubular member. The fluid storage medium prevents premature desorption and off-gassing of the organic contaminants from the side wall of the tubular member until the testing process can be completed. Representative examples of liquid materials which may be used as the fluid storage medium include distilled water, a portion of the water supply being tested, "HPLC-grade" water, and the like. However, the present invention shall not be restricted to any particular fluid storage media compositions.

When the system operator is ready to deliver the carrier gas to the tubular member within the sampling unit in accordance with a preferred embodiment of the invention, the carrier gas is introduced into the gas delivery port of the upper cap member attached to the housing of the sampling unit. Because the first end of the tubular member is operatively connected to the gas delivery port in the upper cap member, the carrier gas rapidly passes into the central passageway of the tubular member (e.g. at an optimum flow rate of about 0.01–1.0 liters/minute). The carrier gas then comes in direct physical contact with the side wall of the tubular member as it flows through the central passageway. This process provides two benefits, namely, (1) it creates a "venturi-effect" in the central passageway which causes the organic contaminants initially absorbed within the side wall of the tubular member to be drawn by suction inwardly into the central passageway instead of diffusing outwardly from the tubular member into the surrounding environment; and (2) it enables the diffused organic contaminants to the collected and "carried" out of the system in an effective manner for subsequent analysis. It should also be noted that the term "deliver" as it applies to introducing of the carrier gas into the tubular member of the sampling unit shall also encompass a situation in which a selected carrier gas is drawn by suction through the tubular member. For example, suction may be applied to the gas exit port in the sampling unit in order to draw a selected carrier gas into the system unit from a source connected to the gas delivery port. In this regard, both of the methods listed above shall be considered equivalent in function and result.

During this stage of the claimed method, the organic contaminants within the side wall of the tubular member pass by diffusion and other related physical processes into the central passageway of the tubular member as noted above. This process takes place in accordance with the unique chemical and physical character of the materials used to construct the tubular member and the negative pressure environment created by the carrier gas. As the organic contaminants pass into the central passageway of the tubular member, they combine with the moving carrier gas to generate a gaseous product comprising the carrier gas combined with the organic contaminants.

The gaseous product is then routed out of the tubular member and sampling unit for analysis. This is accomplished in the present embodiment by passing the gaseous product from the tubular member through the gas exit port in the lower cap member of the sampling unit. As noted above, the second end of the tubular member is operatively connected to the gas exit port in the lower cap member. This arrangement of components enables the gaseous product to be rapidly and efficiently transferred from the central passageway of the tubular member into the gas exit port so that the gaseous product is ultimately removed from the sampling system. The gaseous product is then collected and analyzed to detect the organic contaminants therein. Specifically, the gaseous product is tested using a selected gas analyzer unit to detect, measure, and otherwise characterize the type and quantity of organic contaminant materials in the water supply. The particular type of gas analyzer unit to be employed at this stage will depend on the organic contaminants of interest and other factors, with the claimed process not being restricted to any given analytical system. Further information regarding the collection and characterization procedures associated with the gaseous product will be presented below in the Detailed Description of Preferred Embodiments section.

The present invention enables the testing of a water source/sample to occur in a rapid, accurate, and efficient manner. Likewise, by conducting repeated tests at different locations in the water sample, the claimed method can be used to produce a stratification profile of the contaminants in the water. All of these benefits are achieved using a minimal amount of equipment, personnel, and process steps.

In an alternative embodiment of the claimed method, a testing system is provided which includes multiple sampling units that are simultaneously placed in a water supply at a different location. Each of the sampling units in this multi-unit testing system is identical to the individual sampling unit discussed above. Accordingly, all of the information, parameters, and data previously provided in connection with the sampling unit and testing procedure in the primary embodiment of the claimed process are equally applicable to the present alternative embodiment and are incorporated by reference herein. The use of multiple sampling units which are each positioned within a water supply at a different location enables a stratified, multi-position (vertical or horizontal) contaminant profile of the water source to be obtained in a rapid, simultaneous, and effective manner. The resulting data can then be used to create a pollution "map" of the test site so that proper, site-specific remediation procedures can be accomplished.

Once all of the individual sampling units are placed in the water supply (e.g. at substantially the same time), they are then used to test the water in accordance with the basic procedure outlined above. Gaseous products obtained from each sampling unit (which consist of the carrier gas and organic contaminants from each test zone) are collected and analyzed as previously discussed. Regardless of which analytical approach is used to characterize the contaminant levels in the water supply, the present embodiment enables test data to be obtained in a simultaneous manner from multiple locations in the water source so that a detailed profile of the contaminants in the water can be generated. This is specifically accomplished as indicated above using multiple sampling units which are all positioned at different locations in the water supply, with this method being particularly useful in the testing of deep underground wells.

The present invention represents a significant development in the art of water testing and pollution analysis. Many different processing techniques and materials are encompassed within the basic method of the claimed invention which involves the steps of (A) providing a contaminant-absorbing member made of at least one composition which will absorb organic contaminants directly into the contaminant-absorbing member; (B) immersing the contaminant-absorbing member within the selected water sample so that organic contaminants in the water sample are absorbed into the contaminant-absorbing member; (C) delivering a carrier gas to the contaminant absorbing member so that the carrier gas comes in contact therewith, wherein the organic contaminants pass out of the contaminant-absorbing member and combine with the carrier gas to generate a gaseous product comprising the carrier gas combined with the organic contaminants; and (D) analyzing the gaseous product. Likewise, many benefits are provided by this invention and all of its embodiments including but not limited to: (1) the rapid and efficient testing of water supplies using a minimal amount of energy, equipment, and process steps, with the elimination of complex procedures involving submersible pumps and on site energy (electricity) sources; (2) the ability to test a wide variety of water samples and supplies in situ for many different organic contaminants; (3) elimination of the need to physically withdraw multiple water samples at the test site which eliminates waste accumulation and disposal problems; (4) a high degree of portability which enables testing to occur at remote locations without transporting large amounts of equipment; (5) a reduction in equipment, material, and personnel costs compared with traditional procedures; and (6) the ability to test a water supply at multiple locations in the supply which facilitates the production of a vertical and/or horizontal contaminant profile so that highly effective, site-specific remediation can be achieved. For these reasons and the others listed below, the claimed invention represents an advance in the art of pollution detection and control.

The foregoing discussion of the claimed method and apparatus involves a brief overview of the primary features of the invention. These and other features, objects, and advantages of the invention (as well as a fully-enabling disclosure thereof) shall be provided below in the following Brief Description of the Drawings and Detailed Description of Preferred Embodiments.

DETAILED DESCRIPTION OF PREFERRED EMBODIMENTS

Figure 1:
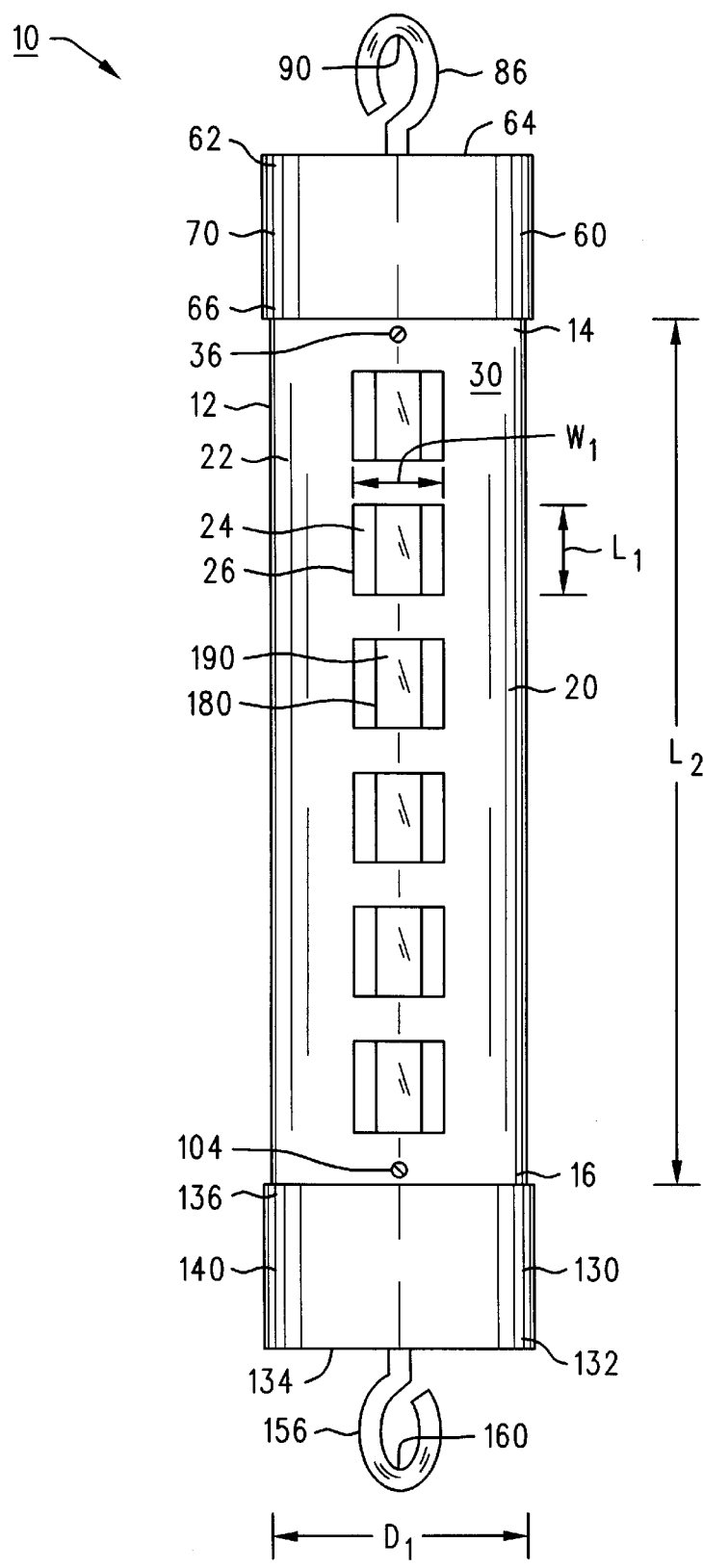
FIG. 1 is a side view of a representative sampling unit manufactured in accordance with the present invention.

The present invention involves a highly-effective method and apparatus for testing underground and above-ground water supplies. Testing is accomplished in a rapid manner which avoids the collection of multiple samples and the disposal problems associated therewith. Instead, one or more sampling units are provided which are directly immersed into the water supply of interest. Each sampling unit includes specially-designed internal components which absorb and retain organic contaminants from the water supply. In accordance with the process described below, the absorbed organic contaminants will subsequently diffuse out of the internal components within the sampling unit. They are then combined with a carrier gas, followed by analysis of resulting gaseous product. This process and a preferred sampling unit will be described in substantial detail below. Likewise, all of the benefits associated with the claimed invention will become readily apparent from the following detailed discussion. In general, the present invention represents a significant development in pollution analysis, with particular emphasis on the detection of organic contaminants.

The claimed sampling apparatus and process shall not be restricted to any particular water supplies which shall also be characterized herein as "water samples". Both above-ground and underground water sources may be tested in situ (e.g. "on-site") with equal effectiveness including but not limited to wells, aquifers, ponds, lakes, streams, creeks, and any other natural or man-made bodies of water. As previously noted, the term "aquifer" basically involves a large underground water supply located within vast regions of rock or soil. It is also contemplated that water samples retained within storage vessels (e.g. tanks) as well as water stored in municipal water towers can be analyzed in accordance with the claimed method. All of these water sources may be tested at any location including factory and mine sites since the claimed invention involves a minimal amount of equipment and operating components.

Likewise, the invention shall not be restricted to any particular materials encompassed within the term "organic contaminants". This term shall involve any carbon-based contaminant compounds which are typically found in water supplies as a result of industrial processes, agriculture, mining, and other activities, with such materials normally being undesired and/or unsafe for consumption by living systems. Of primary concern are materials that are characterized as "volatile organic contaminants (compounds)" or "VOCs". These compositions specifically include halogenated (e.g. chlorinated) solvents such as trichloroethane, dichloroethane, and others. In addition to halogenated solvents, a wide variety of other organic compounds shall be encompassed within the term "organic contaminants" including but not limited to methane, vinyl chloride, ethane, ethene, benzene, xylene, and others. Of equal concern is the presence of petroleum-based fuels (e.g. jet fuel, gasoline, diesel fuel, and the like) in underground water supplies at various transportation-related facilities including gasoline stations, airports, and the like. Regardless of the particular organic contaminants under consideration, the presence of these materials at or near underground and above-ground water supplies is a substantial problem of considerable importance. Accordingly, the present invention shall not be restricted to the analysis of any given organic compounds as noted above. An important feature of the invention involves its ability to detect a wide variety of different materials in many types of water supplies with a minimal amount of equipment, process steps, and labor.

To facilitate a clear and complete understanding of the invention, the following detailed description shall involve these main subject matter categories: (1) A Representative Sampling Unit; (2) The Process of the Present Invention; and (3) An Alternative Embodiment of the Claimed Process.

A. Representative Sampling Unit

A representative sampling unit will now be described in detail with reference to the drawing figures listed above. The present invention shall not be restricted to this particular sampling system which involves a preferred embodiment provided for example purposes. Likewise, the claimed sampling unit shall not be limited to any particular dimensions or construction materials unless otherwise indicated below, with a number of variations being possible in accordance with the intended use of the particular sampling system under consideration.

Figure 2:
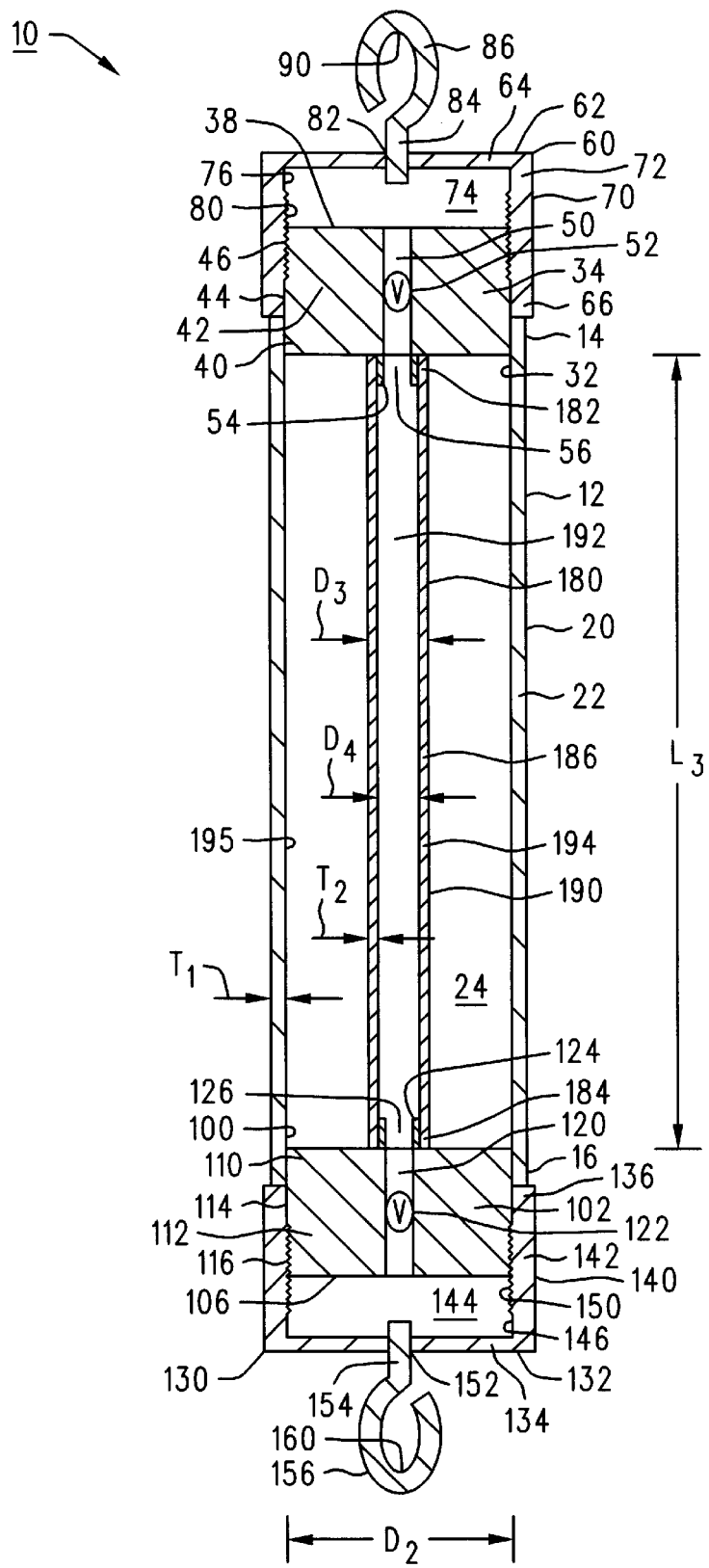
FIG. 2 is a cross-sectional side view of the sampling unit of FIG. 1 illustrating the internal components thereof.

As shown in FIG. 1, a representative sampling unit is disclosed at reference number 10. This sampling unit 10 is elongate in character and is well-suited for use in underground well systems. The sampling unit 10 first includes an exterior housing 12 which is preferably circular in cross-section and tubular in configuration. The housing 12 has an upper end 14, a lower end 16, and a medial portion 20 therebetween. In addition, the housing 12 further comprises an outer wall 22 which surrounds an internal cavity 24 positioned within the housing 12 (FIGS. 1–2). With continued reference to FIG. 1, the outer wall 22 of the housing 12 includes at least one and preferably multiple openings 26 which pass entirely through the housing 12 (e.g. the outer wall 22.) The openings 26 are designed to allow the water samples being tested to flow into the internal cavity 24 of the housing 12 as discussed in greater detail below. The sampling unit 10 shall not be limited to any particular number or grouping of openings 26 which, in a preferred embodiment, are uniformly sized and positioned along the entire exterior surface 30 of the housing 12 from the upper end 14 to the lower end 16. The openings 26 can be circular, square, rectangular, or any other configuration provided that they provide effective access to the internal cavity 24 of the sampling unit 10 and the operating components therein. In a representative and non-limiting embodiment, multiple substantially-square openings 26 are provided as illustrated schematically in FIG. 1. Such openings 26 will typically have a length "$L_1$" and width "$W_1$" ranging from about 0.25–1.0 inches (or a diameter of about 0.25–1.0 inches if circular openings 26 are employed). The individual openings 26 are typically spaced apart from each other by a distance of about 0.125–0.25 inches. However, these numerical parameters are provided for example purposes only, with the present invention not being restricted to openings 26 of any particular number, size, shape or spacing.

Many different construction materials may be employed to produce the housing 12 including but not limited to stainless steel, aluminum, polytetrafluoroethylene [Teflon®], and polyethylene. Likewise, the housing 12 may also be constructed from a mesh or screen material made from metal, plastic, and the like, with the perforations through these materials constituting the openings 26. In a representative, non-limiting, and preferred embodiment, the housing 12 will optimally have an overall length "$L_2$"of about 0.5–5 feet and a diameter "$D_1$"of about 0.5–2.0 inches as shown in FIG. 1. The outer wall 22 will typically have a thickness "$T_1$" (FIG. 2) of about 0.065–0.218 inches, with the internal cavity 24 in the embodiment of FIG. 2 having a uniform diameter "$D_2$" of about 0.546–2.245 inches. However, it is again important to emphasize that the claimed invention shall not be restricted to the above-listed numerical parameters which are provided for example purposes.

With reference to FIG. 2, the upper end 14 of the housing 12 includes a number of structural components which will now be discussed. Specifically, the upper end 14 comprises an upper outlet port 32 which includes a plug-like upper cap member 34 therein that is sized for insertion within the outlet port 32. The cap member 34 may be secured within the outlet port 32 in the housing 12 by a number of different methods including but not limited to frictional engagement between these components, adhesive materials (e.g. epoxy resin or cyanoacrylate compounds known in the art), and/or conventional mechanical fasteners (e.g. screws 36 illustrated in FIG. 1). The upper cap member 34 (as schematically presented in FIG. 2) may involve many different structural configurations other than the design shown in FIG. 2. Likewise, the cap member 34 can be produced from a variety of different construction materials ranging from stainless steel to aluminum, polyethylene, polytetrafluoroethylene [Teflon®], and other similar materials. Regardless of which design configurations and construction materials are employed in connection with the upper cap member 34, it preferably includes a first end 38, a second end 40, a medial section 42, and an outer surface 44. Positioned on the outer surface 44 is an external threaded region 46, the function of which will be outlined below. The second end 40 of the upper cap member 34 is designed for insertion and placement within the outlet port 32 in the housing 12, with the first end 38 and most (or all) of the medial section 42 extending outwardly from the outlet port 32 and housing 12.

Passing entirely through the cap member 34 from the first end 38 to the second end 40 as illustrated in FIG. 2 is an elongate and continuous gas delivery port 50. The gas delivery port 50 is designed to receive a selected carrier gas therein as discussed in substantial detail below. In addition, the gas delivery port 50 may further include at least one optional valve 52 positioned therein (FIG. 2) which is designed to control the flow of materials (e.g. a selected carrier gas) into the internal operating components of the sampling unit 10 as described in the next section. Many different commercially-available valve assemblies may be used as the valve 52 including but not limited to check valves, gas flow control valves, and other automatic or manually-operable valve units known in the art for the purposes set forth herein. Accordingly, the present invention shall not be restricted to the selection and use of any particular structures in connection with the valve 52.

The second end 40 of the upper cap member 34 further comprises an additional structural component which provides an important functional benefit. The second end 40 of the upper cap member 34 specifically includes an outwardly-extending annular section 54 which, in a preferred embodiment, is integrally formed as part of the second end 40. The annular section 54 has a passageway 56 therethrough as illustrated. Again, the purpose of this particular structural component will be discussed below.

With continued reference to FIGS. 1–2, an upper attachment member 60 is provided which includes a closed first end 62 consisting of an end plate 64, a second end 66, and a medial portion 70. Positioned inside the upper attachment member 60 and surrounded by a continuous exterior side wall 72 shown in FIG. 2 is an open interior region 74 which is sized to receive the first end 38 and all (or part) of the medial section 42 of the upper cap member 34. Located on the interior surface 76 of the side wall 72 inside the attachment member 60 (FIG. 2) is an internal threaded region 80. The internal threaded region 80 is designed for threadable engagement with the external threaded region 46 on the outer surface 44 of the upper cap member 34. By placing the first end 38 and all or part of the medial section 42 of the upper cap member 34 within the open interior region 74 of the attachment member 60 and subsequently rotating the attachment member 60 so that both of the threaded regions 46, 80 engage each other, the upper cap member 34 and the attachment member 60 may be secured together.

Finally, the end plate 64 of the attachment member 60 includes an opening 82 therein which is sized to receive the elongate bottom portion 84 of a hook member 86 therein. These components may be attached to each other by welding, adhesive affixation (e.g. using conventional epoxy resin, cyanoacrylate, or other known adhesive compositions), or threadable engagement depending on the construction materials and overall configuration of the above-listed components. The hook member 86 (FIG. 1) further comprises a loop section 90 that is designed to receive an elongate rope-like member therein as discussed further below which may be employed to raise and/or lower the entire sampling unit 10 into a water supply (e.g. an underground well). Accordingly, the attachment member 60 and hook member 86 are primarily designed to connect the sampling unit 10 to a selected system for delivering and extracting the unit 10 from a water source as outlined in the next section. It should also be noted that these components (e.g. the upper attachment member 60 and hook member 86) may be made from many different construction materials, with the present invention not being limited to any particular compositions for this purpose. For example, both of these components can be constructed from stainless steel, aluminum, polytetrafluoroethylene [Teflon®], polyethylene or other comparable materials.

Having described the various components and materials associated with the upper end 14 of the housing 12, the lower end 16 and its structural features will now be summarized. It will become readily apparent from the following discussion and FIG. 2 that the lower end 16 of the sampling unit 10 is substantially identical and symmetrical with the upper end 14. Specifically, the lower end 16 comprises a lower outlet port 100 which includes a plug-like lower cap member 102 therein that is sized for insertion in the outlet port 100. The lower cap member 102 may be secured within the outlet port 100 in the housing 12 using a number of different methods including but not limited to frictional engagement between these components, adhesive materials (e.g. epoxy resin or cyanoacrylate compounds known in the art), and/or conventional mechanical fasteners (e.g. screws 104 shown in FIG. 1). The lower cap member 102 (as schematically illustrated in FIG. 2) may involve many different structural configurations other than the design presented in FIG. 2. Likewise, the cap member 102 can be produced from a wide variety of different construction materials ranging from stainless steel to aluminum, polyethylene, polytetrafluoroethylene [Teflon®], and other comparable materials. In a preferred embodiment, both the upper and lower cap members 34, 102 will be manufactured from the same compositions. Regardless of which design configurations and construction materials are employed in connection with the lower cap member 102, it preferably includes a first end 106, a second end 110, a medial section 112, and an outer surface 114. Positioned on the outer surface 114 is an external threaded region 116, the function of which will be outlined below. The second end 110 of the lower cap member 102 is designed for insertion and placement within the outlet port 100 in the housing 12, with the first end 106 and most (or all) of the medial section 112 extending outwardly from the outlet port 100 and the housing 12.

Passing entirely through the cap member 102 from the first end 106 to the second end 110 is an elongate and continuous gas exit port 120. The gas exit port 120 is primarily used to deliver gaseous materials out of the sampling unit 10 during a testing procedure. As illustrated in FIG. 2, the gas exit port 120 may further comprise at least one optional valve 122 positioned therein which is designed to control the flow of materials (e.g. a selected carrier gas plus collected organic contaminants) out of the sampling unit 10. Many different valve assemblies may be used as the valve 122 including but not limited to check valves, gas flow control valves, and other automatic or manually-operable valve units known in the art for the purposes set forth herein. Accordingly, the present invention shall not be restricted to the selection and use of any particular structures in connection with the valve 122. However, in a preferred embodiment, the valve 122 employed within the gas exit port 120 will be of the same general type as the valve 52 used in the gas delivery port 50.

The second end 110 of the lower cap member 102 further comprises an additional structural component which provides an important functional benefit. The second end 110 of the cap member 102 specifically includes an outwardly-extending annular section 124 which, in a preferred embodiment, is integrally formed as part of the second end 110. The annular section 124 likewise has a passageway 126 therethrough as illustrated. Again, the purpose of this particular structural component will be discussed in greater detail below.

With continued reference to FIGS. 1–2, a lower attachment member 130 is provided which includes a closed first end 132 consisting of an end plate 134, a second end 136, and a medial portion 140. Positioned inside the lower attachment member 130 and surrounded by a continuous exterior side wall 142 as illustrated in FIG. 2 is an open interior region 144 which is sized to receive the first end 106 and all (or part) of the medial section 112 of the lower cap member 102. Located on the interior surface 146 of the side wall 142 inside the lower attachment member 130 (FIG. 2) is an internal threaded region 150. The internal threaded region 150 is designed for threadable engagement with the external threaded region 116 on the outer surface 114 of the lower cap member 102. By placing the first end 106 and all (or part) of the medial section 112 of the lower cap member 102 within the open interior region 144 of the lower attachment member 130 and subsequently rotating the attachment member 130 so that both of the threaded regions 116, 150 engage each other, the lower cap member 102 and the lower attachment member 130 may be secured together.

Finally, the end plate 134 of the attachment member 130 includes an opening 152 therein which is sized to receive the elongate bottom portion 154 of a hook member 156 therein. These components may be attached to each other by welding, adhesive affixation (e.g. using conventional epoxy resin, cyanoacrylate, or other known adhesive compositions), or threadable engagement depending on the construction materials and overall configuration of the above-listed components. The hook member 156 (FIG. 1) further comprises a loop section 160 that is designed to receive an elongate rope-like member (e.g. made of braided metal [stainless steel] cable) therein as discussed further below which may be employed to connect the sampling unit 10 to one or more sequentially-arranged additional sampling units 10. It should also be noted that these components (e.g. the lower attachment member 130 and hook member 156) may be made from many different construction materials, with the present invention not being restricted to any particular compositions for this purpose. For example, both of these components can be produced from stainless steel, aluminum, polytetrafluoroethylene [Teflon®], polyethylene, or other comparable materials. It is preferred that the lower attachment member 130 and hook member 156 be respectively produced from the same compositions used to construct the upper attachment member 60 and hook member 86 associated with the upper end 14 of the housing 12.

The operating components within the internal cavity 24 of the housing 12 will now be described. Of primary concern in the sampling unit 10 is a structure that will directly absorb organic contaminants from the water supply being tested so that these contaminants can be detected and analyzed in accordance with the claimed method. In the embodiments of FIGS. 1–2, this is accomplished through the use of an elongate tubular member 180 positioned within the internal cavity 24 of the housing 12. Access to the tubular member 180 is provided through the openings 26 in the outer wall 22 of the housing 12. The tubular member 180 further includes a first end 182, a second end 184, and a medial section 186 between the first and second ends 182, 184 (FIG. 2). Likewise, the tubular member 180 comprises a continuous, uninterrupted (e.g. non-perforated) side wall 190 and a central passageway 192 through the tubular member 180 which extends continuously from the first end 182 to the second end 184 and is entirely surrounded by the side wall 190. It is an important feature of the claimed invention that the side wall 190 of the tubular member 180 be constructed from at least one composition that will absorb organic contaminants from the water supply directly into the interior region 194 (FIG. 2) of the side wall 190. In a preferred embodiment, this composition shall typically involve any plastic and/or rubber-based materials which are capable of absorbing organic contaminants therein as defined above and subsequently allowing these materials to diffuse (e.g. "off-gas") outwardly from the tubular member 180 in a controlled and detectible manner. Further information regarding this process and the steps which are used to collect and characterize the released organic contaminants will be provided in substantial detail below. However, to accomplish these goals, representative compositions which may be employed to produce the tubular member 180 (which is optimally flexible and of single-piece, unitary construction) include the following materials: polydimethylsiloxane, polytetraflouroethylene (TEFLON®), natural rubber, "latex"-type rubber, polypropylene, polyethylene, nylon, and neoprene. These materials are commercially available from a number of sources including but not limited to the Dow-Corning Company of Midland, Mich. (USA). In the group of compositions listed above, polydimethylsiloxane is preferred which can be obtained from the Dow-Corning Company under the trademark SILASTIC. Nonetheless, the claimed invention shall not be restricted to any particular construction materials in connection with the tubular member 180 provided that they meet the basic qualifications listed above (e.g. that they are capable of absorbing and subsequently releasing on a controlled basis the organic contaminants of interest).

In the embodiment of FIGS. 1–2, the tubular member 180 is linear (substantially straight) in configuration with a representative, non-limiting overall length "$L_3$" of about 0.5–5 feet. The tubular member 180 has a preferred external diameter "$D_3$" (FIG. 2) of about 0.840–2.375 inches. Likewise, the internal diameter "$D_4$" of the central passageway 192 through the tubular member 180 is about 0.125–1.0 inches. Finally, to achieve maximum operational efficiency, the thickness "$T_2$" (FIG. 2) of the side wall 190 associated with the tubular member 180 must be carefully controlled and assessed. The thickness "$T_2$" of the side wall 190 is one important factor which determines the rate at which the organic contaminants of concern defuse out of the tubular member 180. In a preferred and optimum (non-limiting) embodiment involving the construction materials listed above, the uniform thickness "$T_2$" of the side wall 190 is about 0.0235–0.25 inches. Finally, the tubular member 180 will optimally be centered within the internal cavity 24 of the housing 12, with an average distance of about 0.1–1.0 inches being present between the (1) the side wall 190 of the tubular member 180; and (2) the inner surface 195 of the outer wall 22 associated with the housing 12. It is again important to emphasize that the present invention shall not be entirely restricted to the numerical parameters listed above which are provided for example purposes and represent preferred embodiments. Suitable variations to these parameters may be undertaken in accordance with preliminary pilot studies involving many factors including the particular construction materials that are employed in connection with the tubular member 180 and other extrinsic factors.

The tubular member 180 may be connected to and within the housing 12 of the sampling unit 10 in many different ways. However, with particular reference to FIG. 2, mounting of the tubular member 180 in the internal cavity 24 of the housing 12 is specifically accomplished by initially positioning the first end 182 of the tubular member 180 directly adjacent to and against the annular section 54 on the second end 40 of the upper cap member 34. The first end 182 of the tubular member 180 (which is flexible and resilient in accordance with the construction materials listed above) is then urged onto and over the annular section 54 so that the first end 182 is positioned directly on the annular section 54 as illustrated in FIG. 2. These components are maintained together by frictional engagement between the annular section 54 and the tubular member 180 or the use of conventional adhesive materials (e.g. epoxy resins or cyanoacrylate compounds) applied to and between such components. In accordance with this assembly process, the first end 182 of the tubular member 180 is operatively connected to the upper cap member 34, with the central passageway 192 through the tubular member 180 being in fluid communication with (1) the passageway 56 through the annular section 54; and (2) the gas delivery port 50 in the upper cap member 34. This design facilitates the accurate and complete delivery of gaseous materials (e.g. a selected carrier gas) through the upper cap member 34 for ultimate transfer into the central passageway 192 of the tubular member 180 as outlined in the next section.

The second end 184 of the tubular member 180 is operatively connected to and within the internal cavity 24 of the housing 12 in substantially the same manner described above in connection with the first end 182 of the tubular member 180. With continued reference to FIG. 2, second end 184 of the tubular member 180 is initially positioned directly adjacent to and against the annular section 124 on the second end 110 of the lower cap member 102. The second end 184 of the tubular member 180 (which is flexible and resilient in accordance with the construction materials listed above) is then urged onto and over the annular section 124 so that the second end 184 is positioned directly on the annular section 124. These components are maintained in this configuration by frictional engagement between the annular section 124 and the tubular member 180 or the use of conventional adhesive materials (e.g. epoxy resins or cyanoacrylate compounds) applied to and between such components. In accordance with this assembly process, the second end 184 of the tubular member 180 is operatively connected to the lower cap member 102, with the central passageway 192 through the tubular member 180 being in fluid communication with (1) the passageway 126 through the annular section 124; and (2) the gas exit port 120 in the lower cap member 102. This design facilitates the accurate and complete delivery of gaseous materials (e.g. a selected carrier gas plus collected organic contaminants) from the central passageway 192 in the tubular member 180 through the lower cap member 102 for ultimate transfer out of the sampling unit 10.

Figure 3:
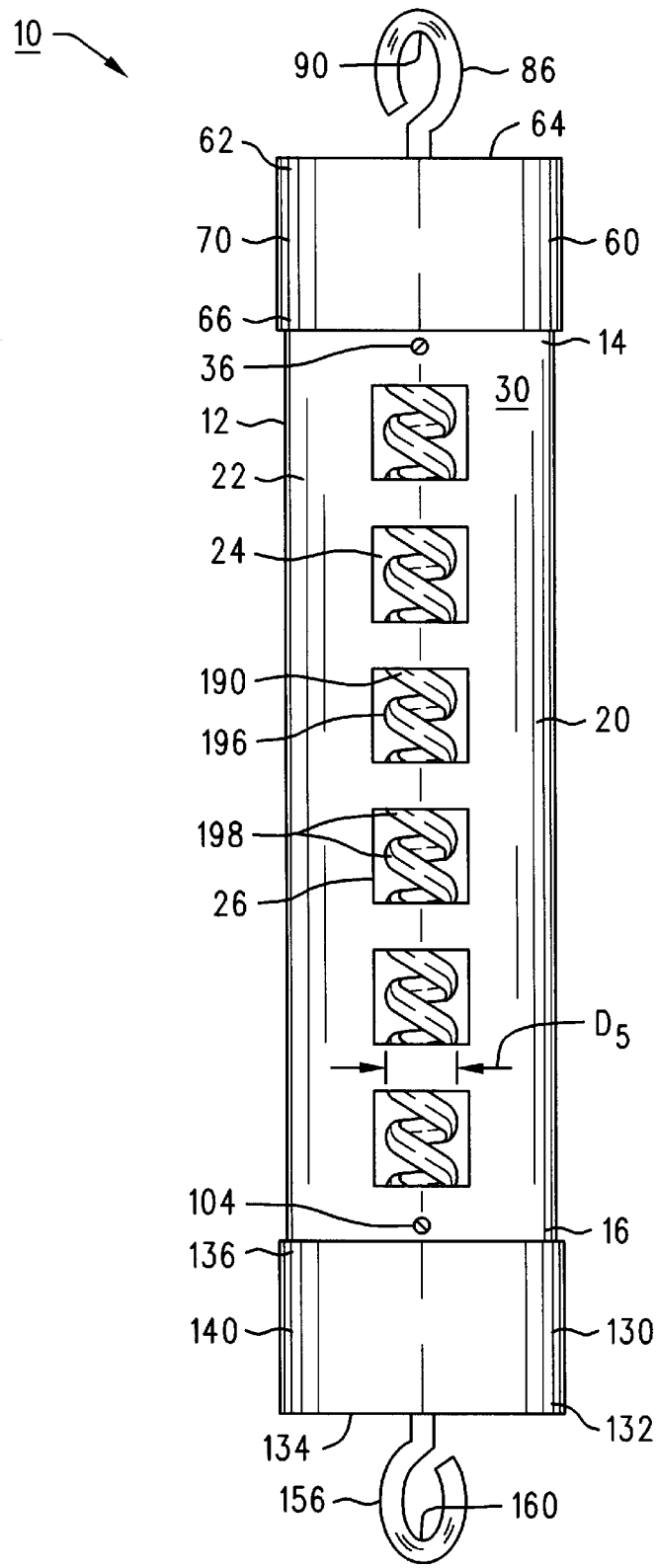
FIG. 3 is a side view of an alternative sampling unit produced in accordance with the invention.

Finally, an alternative embodiment of the sampling unit 10 is illustrated schematically in FIG. 3. All of the parameters, construction materials, dimensions, and operational capabilities associated with the embodiment of FIG. 1 are equally applicable to the embodiment of FIG. 3 unless otherwise indicated below. Reference numbers in FIG. 1 which correspond with those in FIG. 3 signify parts, components, and elements that are common to the structures in both embodiments. These common elements are discussed above in connection with the apparatus of FIG. 1, with the discussion of these items being incorporated by reference relative to the embodiment of FIG. 3. The only difference between the embodiments of FIG. 1 and FIG. 3 is a modification to the shape of the tubular member 180 illustrated in FIG. 1. With reference to FIG. 1, the tubular member 180 is substantially linear (straight) in configuration. In FIG. 3, a modified tubular member 196 is provided which is helically-coiled as illustrated. Specifically, the modified tubular member 196 comprises a plurality of closely grouped helical coils 198 shown schematically in FIG. 3 which, in a preferred embodiment, extend along the entire length of the tubular member 196. This particular design may, in certain circumstances as determined by preliminary testing, provide increased surface area on the tubular member 196 for the enhanced absorbance of organic contaminants into the side wall 190 of the tubular member 196. All of the other parameters associated with the tubular member 196 including its overall length, thickness of the side wall 190, diameter of the central passageway 192, construction materials, and functional capabilities are again the same as those listed above in connection with the tubular member 180 of FIG. 1. Likewise, the modified tubular member 196 is attached in position within the internal cavity 24 of the housing 12 in exactly the same manner as the tubular member 180. It should be noted that, in a preferred embodiment, the helical coils 198 associated with the modified tubular member 196 are each uniformly sized with a representative non-limiting coil diameter "$D_5$" (FIG. 3) of about 0.4–2.0 inches. An operational example of the modified tubular member 196 will also include approximately 1–5 coils per inch. However, the claimed invention shall not be limited to any particular dimensions in connection with the modified tubular member 196 in the alternative embodiment of FIG. 3, with the values listed above being presented for example purposes.

Regardless of the particular design configuration associated with the sampling unit 10, its unique abilities are provided by the following inventive features: (A) the use of a contaminant-absorbing member which is capable of absorbing organic compounds directly into the contaminant-absorbing member; and (B) placement of the contaminant-absorbing member inside a protective housing having multiple water-entry openings through the housing. As a result, the claimed sampling unit is able to effectively detect and characterize organic contaminant levels in a water supply on an in situ basis using the claimed method described below.

B. Process of the Present Invention

Use of the sampling unit 10 to analyze a selected body or sample of water will now be discussed. As previously stated, the claimed method shall not be restricted to the testing of any particular water sources. The terms "water supply" and "water sample" shall encompass underground water supplies (e.g. wells or aquifers as discussed above) and surface water regions (lakes, ponds, streams, creeks, rivers, and the like). Furthermore, the claimed invention shall not be limited to the analysis of any specific organic contaminants. Again, the term "organic contaminant" shall encompass a broad spectrum of organic (carbon-based) compounds including but not limited to alkanes, alkenes, aryl compounds, esters, ethers, halogenated (e.g. chlorinated) derivatives of these materials, petroleum-based compounds (e.g. jet fuel and gasoline), and other comparable materials. The sampling unit 10 and the methods associated therewith not only facilitate testing and analysis of a selected water supply in a rapid and efficient manner, but likewise enable a spatial contaminant distribution to be obtained in which the concentration of a given organic compound can be detected at various pre-determined horizontal or vertical locations in the water supply.

Figure 4:
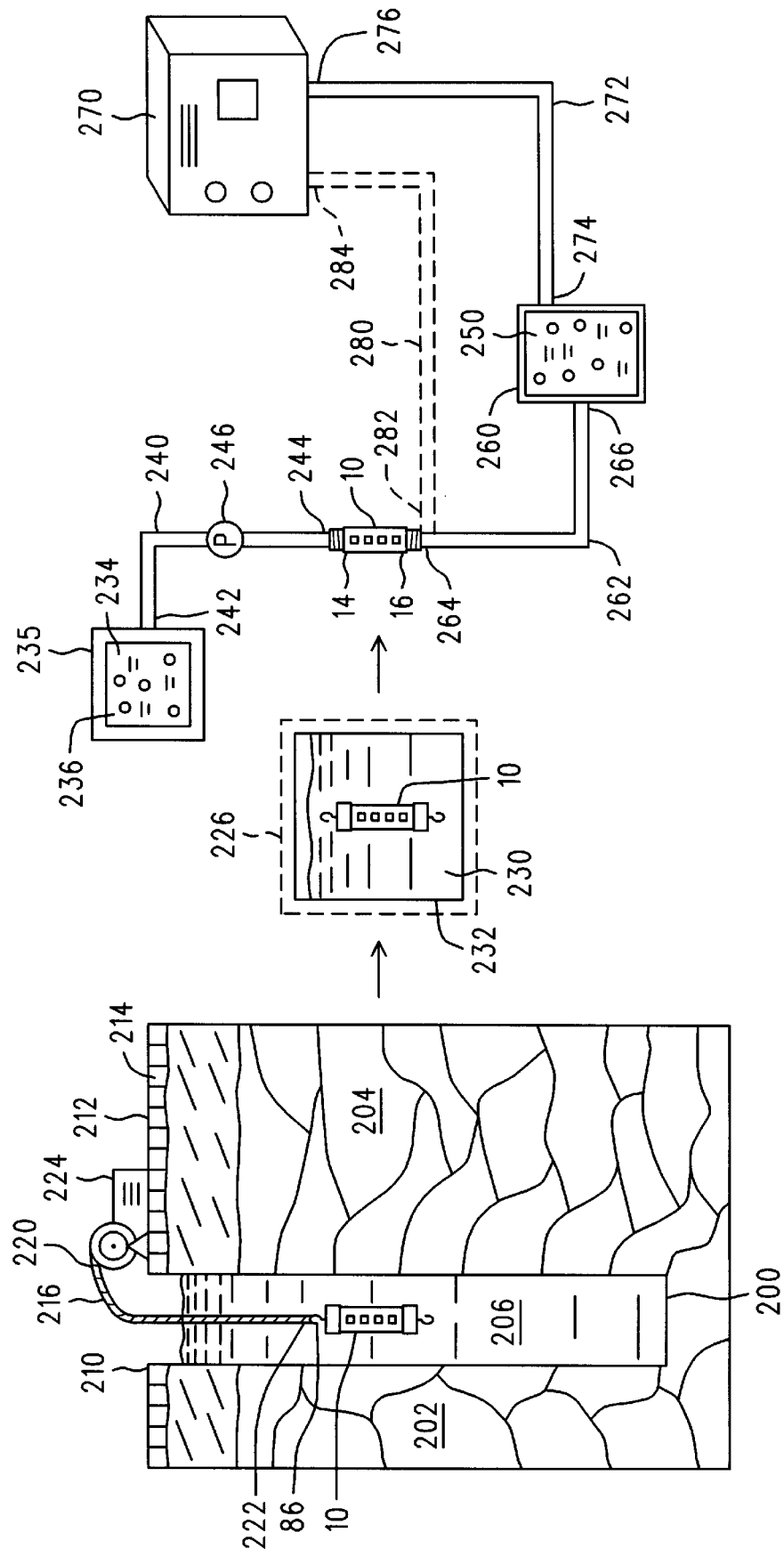
FIG. 4 is a schematic illustration of the steps and materials which are used in the claimed process to detect and measure organic contaminants in a water supply.

With reference to FIG. 4, a representative, schematically-illustrated flow diagram is provided which summarizes the steps, procedures, and materials that are used to analyze a given water source for organic contamination. Unless otherwise indicated, all of the parameters, equipment and other factors associated with the method shown in FIG. 4 and discussed below are provided for example purposes and shall not limit the invention in any respect. In FIG. 4, an underground well 200 is illustrated which is surrounded by adjacent soil regions 202, 204. The well includes a supply of water 206 therein. The well "head" is designated at reference number 210 which is positioned at the upper surface 212 of the surrounding land 214. In the embodiment of FIG. 4, an elongate rope-like cable 216 (preferably made of braided stainless steel) is provided which includes an upper end 220 and a lower end 222. The lower end 222 is operatively connected (e.g. using conventional cable attachment hardware [not shown]) to the loop section 90 of the hook member 86 associated with the upper end 14 of the housing 12 (e.g. to the upper attachment member 60 illustrated in FIG. 1). The upper end 220 of the cable 216 is operatively connected to a motor driven winch apparatus 224 of conventional design. Alternatively, the winch apparatus 224 can be eliminated if desired, with the cable 216 and attached sampling apparatus 10 being moved manually (e.g. by hand) or through the use of a hand-operated system for raising and/or lowering the cable 216 and sampling unit 10. The present invention shall therefore not be restricted to any particular systems or devices for placing the sampling unit 10 in the water 206.

Once the sampling unit 10 is properly oriented (e.g. immersed) within the water 206 in the well 200, the water 206 will flow into the internal cavity 24 inside the housing 12 of the sampling unit 10. The water 206 is able to enter the internal cavity 24 through the openings 26 in the outer wall 22 of the housing 12. As the water 206 enters the internal cavity 24, it comes in direct physical contact with and flows entirely around the tubular member 180. Once the water 206 contacts the side wall 190 of the tubular member 180, organic contaminants in the water 206 will be absorbed directly into the interior region 194 (FIG. 2) of the side wall 190. This situation occurs in accordance with the specific and unique chemical character of the materials described above which are used to produce the tubular member 180. The molecular structure of these materials specifically enables impregnation and diffusion of the organic contaminants into the interior region 194 of the side wall 190. However, the absorbed organic contaminants are only retained within the side wall 190 of the tubular member 180 on a temporary basis. The organic contaminants will ultimately diffuse (e.g. "off-gas") back out of the side wall 190. The remaining steps in the claimed process are designed to effectively collect these materials as they leave the tubular member 180 so that the resulting gaseous product can be analyzed.

In a preferred and non-limiting embodiment, the sampling unit 10 is allowed to remain immersed within the water 206 for a time period of about 8–72 hours so that the complete absorption of organic contaminants into the side wall 190 of the tubular member 180 can take place. It is important to note that this time period can be varied if needed in accordance with preliminary pilot testing. Likewise, the sampling unit 10 which involves the specific construction materials and operational parameters listed above will effectively operate within a broad temperature range (e.g. from about 5–90° C.).

As previously noted, after the organic contaminants are initially absorbed into the side wall 190 of the tubular member 180, they will subsequently "desorb" and diffuse out of the side wall 190 at a slow and controlled rate. It is desired that these materials diffuse in an inward direction toward and into the central passageway 192 of the tubular member 180 where they can later be collected and characterized (as opposed to the passage of these materials outwardly from the side wall 190 into the surrounding external environment). This is effectively accomplished by the next step in the claimed process which represents a unique and important development. Specifically, a supply of at least one carrier gas is delivered (e.g. passed/introduced) into and through the central passageway 192 of the tubular member 180 so that the carrier gas comes in direct contact with the side wall 190 inside the tubular member 180. This process provides two benefits, namely, (1) it creates a "venturi-effect" in the central passageway 192 which causes the organic contaminants initially absorbed within the side wall 190 of the tubular member 180 to be drawn by suction inwardly (instead of outwardly) so that they diffuse into the central passageway 192; and (2) it enables the diffused organic contaminants to be collected and "carried" out of the system in an effective manner for subsequent analysis.

Before a more detailed discussion is provided regarding delivery of the carrier gas into the sampling unit 10, it is important to note that carrier gas delivery is preferably accomplished after the sampling unit 10 is removed from the water source (e.g. the supply of water 206 in the well 200 shown in FIG. 4). However, in certain situations which primarily involve the testing of shallow water supplies that are above ground, delivery of the selected carrier gas to the sampling unit 10 (and removal of the carrier gas plus collected organic contaminants) can occur while the sampling unit 10 remains in situ within the water supply. Either method will provide adequate results although, as noted above, it is preferred that the sampling unit 10 be removed from the water source in order to avoid the need for long gas transfer conduits connected to the sampling unit 10 which can cause pressure reductions and decreases in operating efficiency.

The next step in the claimed process shown in FIG. 4 involves activation of the winch apparatus 224 in order to remove the sampling unit 10 from the water 206 and well 200 (e.g. after passage of the time period listed above). Once the sampling unit 10 is withdrawn from the well 200 using the attached cable 216, the carrier gas can then be delivered to the unit 10. However, before this process takes place, another optional intermediate step may be employed (if needed in accordance with preliminary pilot testing). If any delays are anticipated prior to delivery of the carrier gas to the sampling unit 10, an additional procedure may be initiated to prevent premature desorption/diffusion of the organic contaminants outwardly from the side wall 190 of the tubular member 180 which may occur if testing is significantly delayed (e.g. for more than about 1.0 hour between removal of the sampling unit 10 from the water 206 and introduction of the carrier gas). To accomplish this additional step (which is schematically illustrated in FIG. 4 inside dashed box 226), the sampling unit 10 is placed (e.g. completely immersed) in a selected fluid (liquid) storage medium 230 within a containment vessel 232 prior to delivery of the carrier gas into the central passageway 192 of the tubular member 180. The fluid storage medium prevents premature desorption and off-gassing of the organic contaminants from the side wall 190 of the tubular member 180 until the testing process can be completed. Representative examples of liquid materials which may be used as the fluid storage medium 230 include distilled water, a portion of the water 206 extracted from the well 200, and "HPLC-grade" water. The use of these materials (and the fluid storage medium 230 in general) prevents premature desorption and off-gassing of the organic contaminants from the tubular member 180 by creating a fluid-based pressure barrier which exerts sufficient back-pressure against the side wall 190 of the tubular member 180 to prevent the absorbed organic contaminants from passing out of the tubular member 180. As a result, the integrity of the sampling apparatus 10 is maintained in a highly effective manner.

At this point (whether or not the fluid storage medium 230 is employed), the next step in the claimed process involves delivery (e.g. passage) of the carrier gas into the sampling unit 10. Again, many different methods may be employed to accomplish this goal (depending on the exact configuration of the sampling unit 10), with the present invention not being restricted to any specific procedures and components for this purpose. Immediately prior to gas delivery in the embodiment of FIG. 4, the upper attachment member 60 is removed from the upper cap member 34 by reverse rotation of the attachment member 60 associated with the cap member 34. In a similar manner, the lower attachment member 130 is disengaged from the lower cap member 102. During this time period, the valves 52, 122 (if used) remain in a closed state. Next, as illustrated in FIG. 4, a supply of a selected carrier gas 234 is provided which is retained within a containment vessel 235 having an interior region 236 therein. The containment vessel 235 may be of any type (preferably made of metal) which is suitable for storing gaseous materials. A number of different compositions may be employed in connection with the carrier gas 234 provided that such materials are inert and unreactive in connection with the organic contaminants under consideration as defined above. Representative materials suitable for use as the carrier gas 234 include air, helium, nitrogen, argon, and oxygen. However, the claimed method shall not be restricted to any particular gaseous materials for this purpose. To effectively deliver/introduce the carrier gas 234 to the sampling unit 10, a conduit 240 having a first end 242 and a second end 244 is provided, with the first end 242 being operatively connected to the containment vessel 235 and in fluid communication with the interior region 236 of the vessel 235. The second end 244 of the conduit 240 is operatively connected to and in fluid communication with the sampling unit 10 (e.g. the upper end 14 of the housing 12). To deliver the carrier gas 234 into the tubular member 180 of the sampling unit 10 at a desired flow rate (e.g. about 0.01–1.0 liters/minute in a representative and non-limiting embodiment), an in-line pump 246 is provided within the conduit 240 between the first end 242 and the second end 244. The pump 246 is of a type which is known in the art for gas delivery (e.g. a standard gas-displacement, centrifugal, or other conventional pump system). Alternatively, the pump 246 may be eliminated if the carrier gas 234 is suitably compressed within the containment vessel 235. Either method will provide acceptable results in the present case.

As noted above, the particular chemical and physical characteristics of the materials used to produce the tubular member 180 will cause the organic contaminants that were initially absorbed into the side wall 190 to diffuse out of the tubular member 180. Introduction of the carrier gas 234 into and through the central passageway 192 of the tubular member 180 again provides numerous important benefits, namely, (1) the creation of a "venturi-effect" within the central passageway 192 which causes the organic contaminants to be drawn by suction inwardly (instead of outwardly) so that they diffuse into the central passageway 192; and (2) the production of a "transfer medium" which enables the diffused organic contaminants to the collected and "carried" out of the system in an effective manner for subsequent analysis.

As the carrier gas 234 flows through the conduit 240 toward the housing 12 of the sampling unit 10, it initially enters the gas delivery port 50 of the upper cap member 34. This is accomplished by attachment of the second end 244 of the conduit 240 to and within the gas delivery port 50 at the first end 38 of the upper cap member 34 (FIG. 2) using conventional connection hardware known in the art for conduit attachment. The carrier gas 234 then flows through the valve 52 (which is either manually opened if a non-automatic valve system is employed or opens automatically if a pressure sensitive valve is used), and into the central passageway 192 of the tubular member 180. Gas delivery in this manner is readily accomplished since the first end 182 of the tubular member 180 is operatively connected to the annular section 54 at the second end 40 of the upper cap member 34. As the carrier gas 234 flows through the central passageway 192 of the tubular member 180, it effectively "draws" the organic contaminants within the side wall 190 of the tubular member 180 directly into the central passageway 192. During this unique process, the carrier gas 234 combines with the organic contaminants in the central passageway 192 to produce a gaseous product schematically illustrated at reference number 250 (FIG. 4) which consists of (A) the carrier gas 234 combined with (B) the organic contaminants of concern. As a result, the organic contaminants can be collected and isolated in a highly effective manner.

In a preferred and representative (non-limiting) embodiment, the carrier gas 234 is allowed to flow through the sampling unit 10 (e.g. the central passageway 192 of the tubular member 180) for about 1–25 minutes to ensure that a complete degree of sampling is achieved. However, this particular value (along with the flow rate of the carrier gas 234 into the sampling unit 10) may be varied as needed and desired in accordance with routine preliminary testing involving a number of factors including the particular organic contaminants under consideration, the compositions used to produce the tubular member 180, and other factors of concern. Once the gaseous product 250 is created within the central passageway 192 of the tubular member 180, it travels toward the lower end 16 of the housing 12 (e.g. the lower cap member 102). Thereafter, the gaseous product 250 enters the gas exit port 120 in the lower cap member 102 since the second end 184 of the tubular member 180 is operatively connected to the annular section 124 at the second end 110 of the lower cap member 102. The gaseous product 250 then flows through the gas exit port 120 and valve 122 (which is either manually opened if a non-automatic valve system is employed or opens automatically if a pressure sensitive valve is used), with the gaseous product 250 thereafter leaving the sampling unit 10.

At this stage, the sampling and collection process is completed. However, it should also be noted that the term "deliver" as it applies to introduction of the carrier gas 234 into the tubular member 180 of the sampling unit 10 shall also encompass a situation in which a selected carrier gas 234 is drawn by suction through the tubular member 180. For example, suction may be applied (using a conventional pump-based suction system) to the gas exit port 120 in the sampling unit 10 in order to draw a selected carrier gas 234 into the system from a source connected to the gas delivery port 50. In this regard, both of the methods listed above shall be considered equivalent in function and result.

The resulting gaseous product 250 is then analyzed to detect and otherwise characterize the organic contaminants in the gaseous product 250. Characterization and analysis may be undertaken in many ways, with the claimed method not being restricted to any particular analytical approaches. As shown in FIG. 4, one possible technique involves the operative connection of a selected temporary sample collection container 260 to the lower end 16 of the housing 12 associated with the sampling unit 10. Specifically, a tubular conduit 262 is provided which includes a first end 264 and a second end 266. The first end 264 is operatively connected to the lower end 16 of the housing 12 (e.g. the lower cap member 102) so that the conduit 262 is in fluid communication with the gas exit port 120 in the lower cap member 102. Connection of these components may again be accomplished using conventional connection hardware known in the art for this purpose. The second end 266 of the conduit 262 is operatively connected to the sample collection container 260 schematically illustrated in FIG. 4. While many different sample collection systems may be employed in connection with the container 260, a representative and preferred apparatus for this purpose is known as a "tedlar bag" which is commercially available from SKC Inc. of Eighty Four, PA (USA) and is likewise discussed in U.S. Pat. No. 4,915,356. This apparatus involves a sealed bag unit with a manually-operable valve mechanism associated therewith. Once the gaseous product 250 is in the sample collection container 260 (e.g. the "tedlar bag") it can then be maintained in the container 260 until final analysis is desired. It should be noted that the gaseous product 250 will, in most cases, spontaneously flow into the sample collection container 260 in accordance with the rapidly moving character of the gaseous product 250 as it passes through the sampling unit 10. The gaseous product 250 can then be delivered from the sample collection container 260 to a selected commercially-available gas analyzer unit 270 which is used to analyze the gaseous product 250. In the embodiment of FIG. 4, a tubular conduit 272 is provided which is connected to and between the sample collection container 260 and the gas analyzer unit 270. Specifically, the conduit 272 includes a first end 274 which is operatively connected to the container 260 and a second end 276 that is attached to the gas analyzer unit 270.

However, it should be noted that the sample collection container 260 may be eliminated from the system of FIG. 4, with direct connection of the sampling unit 10 to the gas analyzer unit 270 being employed. The use of a separate sample collection container 260 as discussed above is preferred in situations where water sampling is done off-site at remote locations. In an off-site testing environment, it is more convenient to collect the gaseous product 250 in a separate sample container 260 compared with transporting the gas analyzer unit 270 to the test site. However, in circumstances involving dedicated testing facilities which are constructed at various industrial locations, it may be possible to use a testing system in which the sampling unit 10 is directly connected to the gas analyzer unit 270. This would be accomplished using an additional conduit 280 shown schematically in dashed lines in FIG. 4 which includes a first end 282 and a second end 284. The first end 282 is operatively connected to the lower end 16 of the housing 12 (e.g. the lower cap member 102) using conventional connection hardware so that the conduit 280 is in fluid communication with the gas exit port 120 in the lower cap member 102. Likewise, as illustrated in FIG. 4, the second end 284 of the conduit 280 is attached to the gas analyzer unit 270. Regardless of which transfer method is used (e.g. whether or not a temporary sample collection container 260 is employed), both methods will accomplish a substantially equivalent result, namely, delivery of the gaseous product 250 to the gas analyzer unit 270 in a complete and efficient manner.

At this point, the gas analyzer unit 270 will now be discussed. The claimed process and apparatus of the present invention shall not be restricted to any particular device or system in connection with the gas analyzer unit 270. Many different commercially-available units may be selected for this purpose. For example, representative systems which are suitable for use as the gas analyzer unit 270 include conventional gas chromatograph mass spectrometry units, portable gas chromatographs, photoacoustic infra-red detectors, chlorinated organic vapor monitors, and fourier transform infrared spectrometry units. Commercially available versions of these units include: (1) gas chromatograph mass spectrometry unit produced by the Hewlett-Packard Company of Palo Alto, Calif. (USA)—model no. 5972; (2) a portable gas chromatograph produced by the Sentex Co. of Richfield, N.J. (USA)—model no. "Scentograph Plus-II"; (3) a photoacoustic infra-red detector produced by the Bruel Kjar Co. of Denmark—model no. 1302; (4) a chlorinated organic vapor monitor produced by TSI Incorporated of St. Paul, Minn. (USA)—model no. "RCL"; and (5) a fourier transform infrared spectrometry unit by the Midac Company. All of these systems are highly sensitive, and are able to provide accurate quantitative and qualitative information involving the contaminant materials in the gaseous product 250. The selection of any given system in connection with the gas analyzer unit 270 will depend on a variety of factors as determined by routine pilot investigations involving a number of factors including the particular type of contaminant(s) under consideration.

Operation of the gas analyzer unit 270 will indicate in an effective manner the amount and type of organic contaminants in the gaseous product 250. The basic operative principle in the claimed method involves a relationship in which the concentration of organic contaminants in the gaseous product 250 is directly proportional to the degree of contamination in the water supply being tested. This information is obtained without the complex equipment and procedures associated with prior testing systems, and without any need to actually remove water samples from a test site (which can create substantial disposal problems.) In addition, to assist in the analysis and characterization of a given gaseous product 250, a preliminary calibration curve may be obtained by using the sampling unit 10 and testing procedure described above to analyze "control" water samples which are formulated to have predetermined amounts of a desired contaminant therein. By using these "control" samples to generate a standardized calibration curve, this information may then be employed to accurately assess the amount of contaminants in an "unknown" water sample.

As a final note, once the testing process is finished, the sampling unit 10 may be reused as often as desired since substantially all of the previously-absorbed organic compounds in the tubular member 180 will have diffused out of the system in accordance with the particular chemical characteristics of the materials used to construct the tubular member 180. Regardless of the specific manner in which the claimed process is implemented, the general concept of the present invention represents an important development in the field of contaminant analysis, with this basic procedure involving the steps of: (1) providing a contaminant-absorbing member comprised of at least one composition which will absorb organic contaminants directly into the contaminant-absorbing member; (2) immersing the contaminant-absorbing member within a water sample so that any organic contaminants within the water sample are absorbed into the contaminant-absorbing member; (3) delivering a carrier gas to the contaminant-absorbing member so that the carrier gas comes in contact therewith, wherein the organic contaminants pass out of the contaminant-absorbing member and mix with the carrier gas to generate a gaseous product comprising the carrier gas combined with the organic contaminants; and (4) analyzing the gaseous product to detect the organic contaminants therein. This unique process constitutes a significant technical development which provides the many benefits listed above. In addition, the claimed method is capable of detecting organic contaminants in water supplies at a level as low as about 1.0 $\mu$g/liter in most cases.

C. Alternative Embodiment of the Claimed Process

Figure 5:
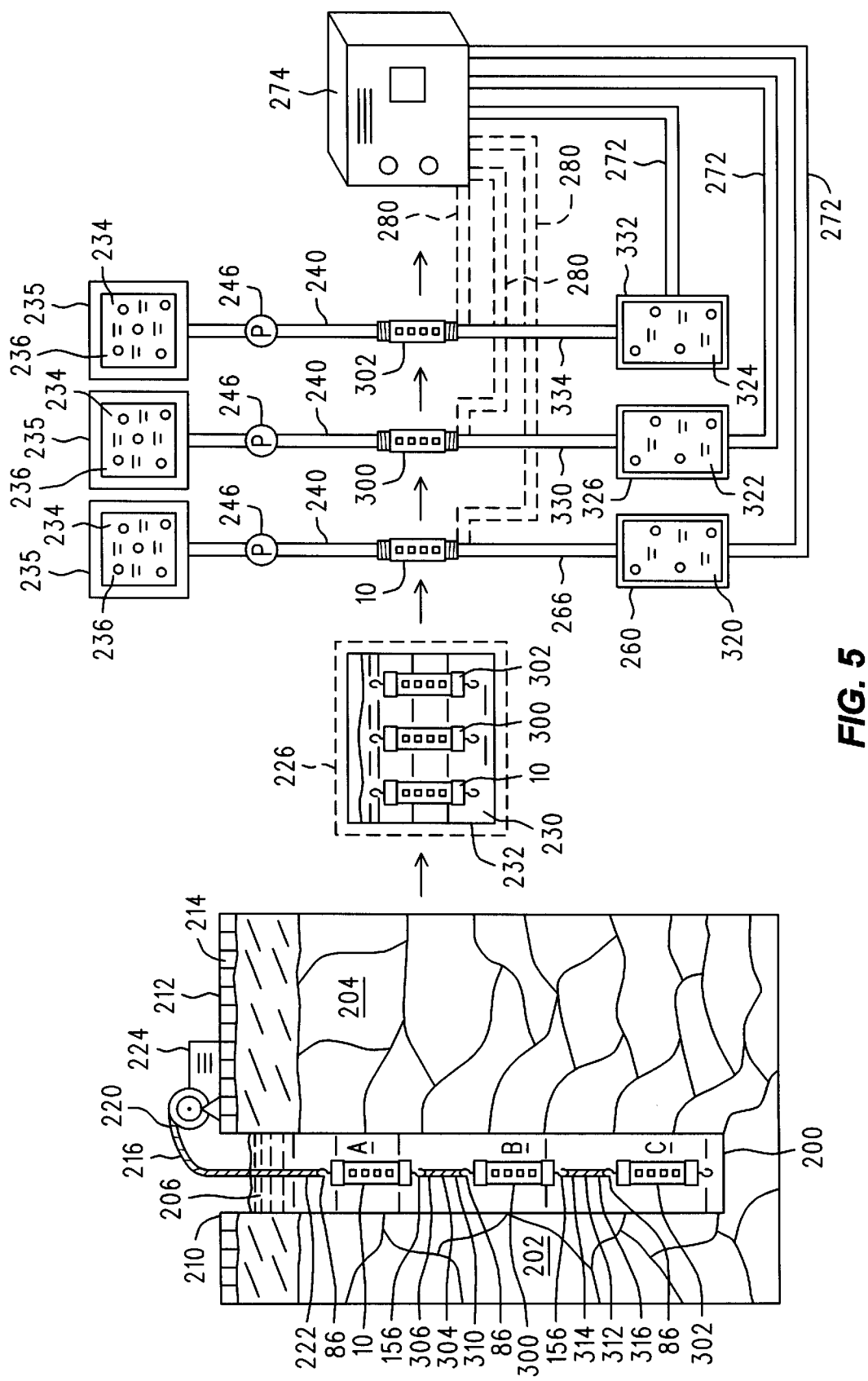
FIG. 5 is a schematic illustration of the steps and materials which are used in an alternative embodiment of the claimed process to detect and measure organic contaminants in a water supply.

Finally, an alternative embodiment of the claimed process is schematically illustrated in FIG. 5. In the embodiment of FIG. 5, a testing system is provided which includes multiple sampling units that are all placed in a water supply at substantially the same time but at different locations in the water. Each of the sampling units in this multi-unit testing system is identical to the individual sampling unit 10 discussed above. Accordingly, all of the information, parameters, and data previously provided in connection with the sampling unit 10 and testing procedures in the primary embodiment of the claimed process are equally applicable to the present alternative embodiment and are incorporated by reference herein. The use of multiple sampling units which are each positioned within a water supply at a different location enables a multi-position contaminant profile of the water supply to be obtained in a rapid, simultaneous, and effective manner. The resulting data can then be used to create a pollution "map" of the test site so that site-specific remediation procedures can be accomplished.

With reference to FIG. 5, the alternative sampling process described above is schematically illustrated in which a plurality of individual sampling units are simultaneously positioned in the well 200 (e.g. all at substantially the same time). In addition to the original sampling unit 10 which is located at position "A" in the water 206, additional sampling units 300, 302 are provided. Sampling unit 300 is located below sampling unit 10 (at position "B"), while sampling unit 302 is provided at position "C" beneath sampling unit 300 in order to form a "chain" of successive sampling units 10, 300, 302. This group of sampling units 10, 300, 302 is capable of generating an accurate vertical profile of contamination levels in the water 206. All of the sampling units 10, 300, 302 are identical to each other, with the description of sampling unit 10 provided above (as well as the illustration of sampling unit 10 in FIGS. 1–2) being equally applicable to all of the sampling units 10, 300, 302 in this embodiment. For example, the side wall 190 of the tubular member 180 in each of the sampling units 10, 300, 302 will have a preferred thickness "$T_2$" (FIG. 2) of about 0.0235–0.25 inches, with the other parameters listed above also being applicable to all three sampling units 10, 300, 302 (including the use of either a linear or helically-coiled tubular member 180).

Regarding connection of the sampling units 10, 300, 302 to each other, the sampling unit 10 is attached to the lower end 222 of cable 216 (which is preferably made of braided stainless steel cable as previously indicated). Specifically, the lower end 222 is operatively connected (e.g. using conventional cable attachment hardware [not shown]) to the loop section 90 of the hook member 86 secured to the upper end 14 of the housing 12. The upper end 220 of the cable 216 is connected to the winch apparatus 224 as previously discussed. A first additional cable section 304 (e.g. made of braided stainless steel) is then provided between the sampling unit 10 and the sampling unit 300 with the cable section 304 including an upper end 306 and a lower end 310. The upper end 306 of the cable section 304 is operatively connected using conventional cable connection hardware to the loop section 160 of the hook member 156 secured to the lower end 16 of the housing 12. Likewise, with continued reference to FIG. 5, the lower end 310 of the cable section 304 is operatively connected using conventional cable connection hardware to the loop section 90 of the hook member 86 secured to the upper end 14 of the housing 12 associated with the sampling unit 300. In this manner, the sampling unit 10 is linked to the sampling unit 300 using the cable section 304.

As further shown in FIG. 5, a second additional cable section 312 (e.g. made from braided stainless steel) is provided between the sampling unit 300 and the sampling unit 302. The cable section 312 further includes an upper end 314 and a lower end 316. The upper end 314 of the cable section 312 is operatively connected using conventional cable connection hardware to the loop section 160 of the hook member 156 secured to the lower end 16 of the housing 12 associated with the sampling unit 300. Likewise, the lower end 316 of the cable section 312 is operatively connected using conventional cable connection hardware to the loop section 90 of the hook member 86 secured to the upper end 14 of the housing 12 associated with the sampling unit 302. In this manner, the sampling unit 300 is linked to the sampling unit 302 using the cable section 312. While the linkage method described above is preferred and highly effective, the claimed invention shall not be restricted to any particular procedure for attaching the multiple sampling units 10, 300, 302 together in this embodiment. Other attachment methods may be employed with equal effectiveness including the use of separate cable members (not shown) for each sampling unit 10, 300, 302.

The sampling units 10, 300, and 302 are then used to measure water contamination levels in the same manner discussed above in connection with the embodiment of FIG. 4. Specifically, the sampling units 10, 300, 302 are all immersed within the water 206 at substantially the same time and are all removed from the water 206 simultaneously (if removal is part of the desired process). It is again preferred that all of the sampling units 10, 300, 302 be maintained within the water 206 for the same time period listed above (e.g. about 8–72 hours) and thereafter removed as a group. Alternatively, the sampling units 10, 300, 302 may be further processed (e.g. supplied with a selected carrier gas) while being maintained within the water 206 as discussed above in the primary embodiment.

A carrier gas is then delivered into each sampling unit 10, 300, 302 as previously described in the embodiment of FIG. 4 (e.g. using same operational parameters including a preferred and non-limiting gas flow rate of about 0.01–1.0 liters/minute over a time period of about 1–25 minutes for each sampling unit 10, 300, 302). These parameters may be varied as needed in accordance with preliminary pilot studies. With continued reference to FIG. 5, it should also be noted that, when the sampling units 10, 300, 302 are removed from the water 206 and well 200, they may immediately be supplied with the carrier gas or, if a delay is needed or desired, they can be placed within the containment vessel 232 having a fluid storage medium 230 therein of the type listed above.

When delivery (e.g. passage/introduction) of the carrier gas into the sampling units 10, 300, 302 is desired, each of the sampling units 10, 300, 302 is attached to the containment vessel 235 having the carrier gas 234 therein (FIG. 5) so that the carrier gas 234 can be transferred into the sampling units 10, 300, 302 as discussed above in the first embodiment of the invention. Each of the sampling units 10, 300, 302 can be sequentially attached to the single containment vessel 235 using the conduit 240 in order to produce a gaseous product in each unit 10, 300, 302. Likewise, if desired, each of sampling units 10, 300, 302 can be connected to a separate containment vessel with an individual supply of carrier gas therein to further expedite the testing process. Both methods shall be considered equivalent to each other in function and result. Also, the carrier gas 234 can be transferred into the sampling units 10, 300, 302 as discussed above or, in the alternative, passed through each sampling unit 10, 300, 302 by suction as previously noted. Both methods of delivering the carrier gas 234 into and through the sampling units 10, 300, 302 shall therefore be deemed equivalent.

Once the carrier gas 234 has passed into each of the sampling units 10, 300, 302, a separate gaseous product is obtained from each unit 10, 300, 302. For, example, a primary gaseous product 320 is isolated from sampling unit 10, with sampling unit 300 producing a secondary gaseous product 322. Sampling unit 302 will likewise yield a tertiary gaseous product 324. As shown in FIG. 5, each of the gaseous products 320, 322, 324 may be delivered into a separate temporary sample collection container such as the "tedlar bag" mentioned above which is commercially available from SKC Inc. of Eighty Four, PA (USA). With reference to FIG. 5, sampling unit 10 is operatively connected to the sample collection container 260 via conduit 262 as previously discussed. In a similar manner, the sampling unit 300 is attached to a separate sample collection container 326 of the same type as container 260 via tubular conduit 330. Finally, sampling unit 302 is connected to another sample collection container 332 of the same type as container 260 via tubular conduit 334. In this embodiment, it is important that all of the sample collection containers 260, 326, and 332 be maintained separately so that each gaseous product 320, 322, 324 can be individually analyzed. It should also be noted that, if necessary, only a single sample collection container (e.g. container 260) may be used in the system of FIG. 5 if the contents of the container 260 are repeatedly tested and removed from the container 260 on a sequential basis, thereby making the container 260 available for multiple testing procedures.

Finally, each of the sample collection containers 260, 326, 332 in the embodiment of FIG. 5 may be sequentially connected to the gas analyzer unit 274 discussed above (using the conduit 272) in order to analyze each gaseous product 320, 322, 324. It should likewise be understood that, in the alternative, the gas analyzer unit 274 may be directly and sequentially connected to each of the sampling units 10, 300, 302 without using the temporary sample collection containers 260, 326, 332 depending on the testing environment and other circumstances as determined by preliminary testing. For example, the gas analyzer unit 274 can be directly connected to the sampling units 10, 300, 302 using conduit 280 as noted above and shown in dashed lines in FIG. 5.

Use of the gas analyzer unit 274 (and the different devices which may be employed for this purpose) are discussed in detail above. Regardless of which analytical approach is employed to characterize the contaminant levels in the water 206, the present embodiment enables test data to be obtained in a simultaneous manner from multiple locations in the water 206 so that a detailed in situ profile of the contaminants can be produced. For example, data derived from gaseous product 320 can be used to characterize organic contaminant levels in the water 206 at position "A" (FIG. 5) within the well 200. The data obtained from the gaseous product 322 will provide information regarding the chemical content of the water 206 at position "B". Finally, information received from the gaseous product 324 will provide important data involving organic contaminants in the water 206 at position "C". In this manner, a vertical contaminant profile of the water 206 can be generated in a minimal amount of time without repeated sampling steps.

It is important to emphasize that this embodiment of the claimed process shall not be limited to any particular number of sampling units which may be simultaneously deployed in the selected water sample, and shall likewise not be restricted to any particular type of organic contaminants, water supplies, or sampler location (vertical or horizontal) in the water source.

As previously discussed, the present invention offers numerous benefits and advantages including: (1) the rapid and efficient testing of water supplies using a minimal amount of energy, equipment, and process steps, with the elimination of complex procedures involving submersible pumps; (2) the ability to test a wide variety of water samples and supplies in situ for many different organic contaminants; (3) elimination of the need to physically withdraw multiple water samples at the test site which eliminates waste accumulation and disposal problems; (4) a high degree of portability which enables testing to occur at remote locations without transporting large amounts of equipment; (5) a reduction in equipment, material, and personnel costs compared with traditional procedures; and (6) the ability to test a water supply at multiple locations in the supply which facilitates the production of a vertical and/or horizontal contaminant profile so that site-specific remediation can be achieved. For these reasons, the claimed invention represents a significant advance in the art of pollution detection and control. Having herein set forth preferred embodiments of the invention, it is anticipated that suitable modifications may be made thereto by individuals skilled in the art which nonetheless remain within the scope of the invention. For example, the invention shall not be limited to any size parameters, gas analyzer units, hardware, and other similar items. In this regard, the present invention shall only be construed in accordance with the following claims:

We claim:

1. A method for measuring and detecting organic contaminants within a water sample comprising:

providing a contaminant-absorbing member comprised of a composition which will absorb said organic contaminants directly into said contaminant-absorbing member during use of said contaminant-absorbing member;

immersing said contaminant-absorbing member within said water sample so that said organic contaminants within said water sample are absorbed into said contaminant-absorbing member;

removing said contaminant-absorbing member from said water sample;

placing said contaminant-absorbing member into a fluid storage medium, said fluid storage medium preventing desorption and premature off-gassing of said organic contaminants from said contaminant-absorbing member prior to removal of said organic contaminants from said contaminant-absorbing member;

delivering a supply of at least one carrier gas to said contaminant-absorbing member so that said carrier gas comes in contact therewith, said organic contaminants passing out of said contaminant-absorbing member and combining with said carrier gas to generate a gaseous product comprising said carrier gas in combination with said organic contaminants; and analyzing said gaseous product to detect said organic contaminants therein.

2. A method for measuring and detecting organic contaminants within a water sample comprising:

providing a sampling unit for measuring and detecting said organic contaminants in said water sample, said sampling unit comprising:

a housing comprising an outer wall and an internal cavity therein surrounded by said outer wall, said outer wall comprising at least one opening therethrough which enables said water sample to pass through said outer wall and into said internal cavity of said housing during use of said sampling unit, said housing further comprising an upper end and a lower end;

an upper cap member secured to said upper end of said housing, said upper cap member comprising a gas delivery port therethrough;

a lower cap member secured to said lower end of said housing, said lower cap member comprising a gas exit port therethrough; and a tubular member positioned within internal cavity of said housing, said tubular member comprising a first end, a second end, a side wall having a thickness of about 0.0235–0.25 inches, and a central passageway therein surrounded by said side wall, said side wall being comprised of a composition which will absorb said organic contaminants directly into said side wall of said tubular member, said first end of said tubular member being operatively connected to said upper cap member so that said central passageway through said tubular member is in fluid communication with said gas delivery port, with said second end of said tubular member being operatively connected to said lower cap member so that said central passageway through said tubular member is in fluid communication with said gas exit port;

immersing said sampling unit within said water sample, said water sample flowing into said internal cavity of said housing through said opening in said outer wall of said housing and thereafter coming in contact with said tubular member in said housing so that said organic contaminants within said water sample are absorbed into said side wall of said tubular member, said sampling unit being maintained within said water sample for about 8–72 hours;

removing said sampling unit from said water sample after said immersing of said sampling unit within said water sample;

placing said sampling unit into a fluid storage medium after said removing of said sampling unit from said water sample, said fluid storage medium preventing desorption and premature off-gassing of said organic contaminants from said side wall of said tubular member prior to removal of said contaminants from said sampling unit;

delivering a supply of at least one carrier gas into said gas delivery port of said upper cap member of said sampling unit so that said carrier gas passes into and through said central passageway of said tubular member at a flow rate of about 0.01–1.0 liters/minute for a time period of about 1–25 minutes, said organic contaminants passing out of said side wall of said tubular member and into said central passageway of said tubular member during said delivering of said carrier gas thereto in order to generate a gaseous product comprising said carrier gas in combination with said organic contaminants;

passing said gaseous product through said gas exit port in said lower cap member of said sampling unit so that said gaseous product is removed from said central passageway of said tubular member; and analyzing said gaseous product to detect said organic contaminants therein.

3. A method for measuring and detecting organic contaminants in a water sample comprising:

providing a sampling system comprising a plurality of sampling units for measuring and detecting said organic contaminants in said water sample, each of said sampling units comprising
a tubular member therein, said tubular member comprising a side wall and a central passageway therethrough surrounded by said side wall, said side wall being comprised of a composition which will absorb said organic contaminants directly into said side wall of said tubular member;

immersing all of said sampling units into said water sample with each of said sampling units being placed at a different location within said water sample, said water sample coming in contact with said tubular member in each of said sampling units so that said organic contaminants within said water sample will be absorbed into said side wall of said tubular member in each of said sampling units;

removing said sampling units from said water sample after said immersing of said sampling units within said water sample;

placing said sampling units into fluid storage medium after said removing of said sampling units from said water sample, said fluid storage medium preventing desorption and premature off-gassing of said organic contaminants from said side wall of said tubular member in each of said sampling units prior to removal of said contaminants from said sampling units;

delivering a supply of at least one carrier gas into and through said central passageway of said tubular member in each of said sampling units, said organic contaminants passing out of said side wall of said tubular member and into said central passageway of said tubular member during said delivering of said carrier gas thereto in order to generate a gaseous product within each of said sampling units comprising said carrier gas in combination with said organic contaminants; and analyzing said gaseous product from each of said sampling units to detect said organic contaminants therein and produce a distribution profile of said organic contaminants in said water sample.

4. A method for measuring and detecting organic contaminants within a water supply which is located within the ground and beneath the surface thereof comprising:

providing a water supply positioned within said ground and beneath said surface thereof;

providing a sampling unit for measuring and detecting said organic contaminants in said water supply, said sampling unit comprising a tubular member therein, said tubular member comprising a side wall and a central passageway therethrough surrounded by said side wall, said side wall being comprised of a composition which will absorb said organic contaminants directly into said side wall of said tubular member;

lowering said sampling unit into said ground beneath said surface thereof so that said sampling unit is positioned within said water supply, said water supply coming in contact with said tubular member;

leaving said sampling unit within said water supply in said ground for a time period sufficient to enable said organic contaminants in said water supply to be absorbed into said side wall of said tubular member, said water supply remaining within said ground during absorption of said organic contaminants into said side wall of said tubular member;

removing said sampling unit from said ground after passage of said time period so that said sampling unit is withdrawn from said water supply;

placing said sampling unit into a fluid storage medium after said removing of said sampling unit from said ground, said fluid storage medium preventing desorption and premature off-gassing of said organic contaminants from said side wall of said tubular member prior to removal of said contaminants from said sampling unit;

delivering a supply of at least one carrier gas into and through said central passageway of said tubular member, said organic contaminants passing out of said side wall of said tubular member and into said central passageway of said tubular member during said delivering of said carrier gas thereto in order to generate a gaseous product comprising said carrier gas in combination with said organic contaminants; and analyzing said gaseous product to detect said organic contaminants therein.

5. The method of claim 4 wherein said sampling unit further comprises a housing comprising an upper end, a lower end, an outer wall, and an internal cavity therein surrounded by said outer wall, said tubular member being Positioned within said internal cavity, said outer wall comprising at least one opening therethrough which enables said water supply to pass through said outer wall and into said internal cavity of said housing during use of said sampling unit, said sampling unit further comprising an upper cap member secured to said upper end of said housing and a lower cap member secured to said lower end of said housing, said upper cap member comprising a gas delivery port therethrough and said lower cap member comprising a gas exit port therethrough, said tubular member in said housing further comprising a first end and a second end, said first end of said tubular member being operatively connected to said upper cap member so that said central passageway through said tubular member is in fluid communication with said gas delivery port, with said second end of said tubular member being operatively connected to said lower cap member so that said central passageway through said tubular member is in fluid communication with said gas exit port, said delivering of said carrier gas into and through said central passageway of said tubular member comprising introducing said carrier gas into said gas delivery port in said upper cap member, said carrier gas passing from said gas delivery port into said central passageway of said tubular member to form said gaseous product, said gaseous product thereafter passing out of said central passageway of said tubular member through said gas exit port in said lower cap member.

6. The method of claim 4 wherein said tubular member in said sampling unit is comprised of polydimethylsiloxane.

7. The method of claim 4 wherein said side wall of said tubular member in said sampling unit has a thickness of about 0.0235–0.25 inches.

8. The method of claim 4 wherein said tubular member in said sampling unit is elongate and helically coiled in order to provide increased surface area on said tubular member for enhanced absorbance of said organic contaminants.

9. The method of claim 4 wherein said sampling unit is maintained within said water supply during said delivering of said carrier gas into and through said central passageway of said tubular member.

10. The method of claim 4 wherein said carrier gas is selected from the group consisting of air, helium, nitrogen, argon, and oxygen.

11. The method of claim 4 wherein said delivering of said carrier gas into and through said central passageway of said tubular member comprises passing said carrier gas into and through said central passageway at a flow rate of about 0.01–1.0 liters/minute.

12. The method of claim 4 wherein said delivering of said carrier gas into and through said central passageway of said tubular member occurs for a time period of about 1–25 minutes.

13. The method of claim 4 further comprising removing said sampling unit from said ground and said water supply therein prior to said delivering of said carrier gas into and through said central passageway of said tubular member.

14. The method of claim 4 wherein said time period sufficient to enable said organic contaminants in said water supply to be absorbed into said side wall of said tubular member is about 8–72 hours.

* * * * *